US011534517B2

(12) United States Patent
Herrig et al.

(10) Patent No.: US 11,534,517 B2
(45) Date of Patent: Dec. 27, 2022

(54) WICKING PAD FOR EVAPORATING FLUIDS IN A STERILIZER

(71) Applicant: Medivators Inc., Minneapolis, MN (US)

(72) Inventors: Judson A. Herrig, Elko New Market, MN (US); Adam Zutz, Minneapolis, MN (US)

(73) Assignee: Medivators Inc., Minneapolis, MN (US)

( * ) Notice: Subject to any disclaimer, the term of this patent is extended or adjusted under 35 U.S.C. 154(b) by 168 days.

(21) Appl. No.: 16/849,511

(22) Filed: Apr. 15, 2020

(65) Prior Publication Data

US 2020/0330633 A1  Oct. 22, 2020

Related U.S. Application Data

(60) Provisional application No. 62/835,617, filed on Apr. 18, 2019.

(51) Int. Cl.
*A61L 2/20* (2006.01)
*A61L 2/26* (2006.01)

(52) U.S. Cl.
CPC .......... *A61L 2/208* (2013.01); *A61L 2/20* (2013.01); *A61L 2/204* (2013.01); *A61L 2/26* (2013.01); *A61L 2202/11* (2013.01); *A61L 2202/122* (2013.01); *A61L 2202/15* (2013.01); *A61L 2202/24* (2013.01)

(58) Field of Classification Search
CPC . A61L 2/18; A61L 2/183; A61L 2/186; A61L 2/20; A61L 2/204; A61L 2/206; A61L 2/208; A61L 2/24; A61L 2/26; A61L 2202/11; A61L 2202/12; A61L 2202/122; A61L 2202/15; A61L 2202/24
See application file for complete search history.

(56) References Cited

U.S. PATENT DOCUMENTS 9,421,292 B2 * 8/2016 Parker .................. A61B 50/30
2021/0023250 A1 * 1/2021 Golkowski ............ A61L 2/202

* cited by examiner

*Primary Examiner* — Timothy C Cleveland

(57) ABSTRACT

A decontamination system, method, and sterilant kit for a device, such as a lumen device, is depicted. The decontamination system, in some embodiments, includes a device container, a wicking pad, and a sterilant fluid delivery device. The device container, such as a terminal package or a decontamination chamber, defines a device receiving area. The wicking pad is in fluid communication with the device receiving area. The sterilant fluid delivery device is in fluid communication with the wicking pad. The sterilant fluid delivery device is configured to wet the wicking pad with sterilant fluid. The wicking pad is configured to evaporate sterilant fluid into the device receiving area.

20 Claims, 3 Drawing Sheets

WICKING PAD FOR EVAPORATING FLUIDS IN A STERILIZER

PRIORITY CLAIM

This application claims priority to and benefit of U.S. Provisional Application with Ser. No. 62/835,617 filed Apr. 18, 2019, entitled WICKING PAD FOR EVAPORATING FLUIDS IN A STERILIZER, which is herein incorporated by reference in its entirety.

TECHNICAL FIELD

This disclosure relates generally to decontamination of devices such as medical devices; in particular, this disclosure relates to a wicking pad for delivering fluid in a sterilizer through evaporation.

BACKGROUND

Robust instruments such as medical instruments are often sterilized at high temperatures. Commonly, the instruments are sterilized in a steam autoclave under a combination of high temperature and pressure. While such sterilization methods are very effective for more durable medical instruments, advanced medical instruments formed of rubber and plastic components with adhesives are delicate and wholly unsuited to the high temperatures and pressures associated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

Endoscopes can also present problems in that such devices typically have numerous exterior crevices and interior lumens which can harbor microbes. Microbes can be found on surfaces in such crevices and interior lumens as well as on exterior surfaces of the endoscope. Other medical or dental instruments which comprise lumens, crevices, and the like can also provide challenges for decontaminating various internal and external surfaces that can harbor microbes.

Existing decontamination systems introduce sterilant fluid through spray nozzles to aerosolize the fluid. This coats the interior surface of the machine and/or sensors with the sterilant fluid. After decontamination, however, stabilizers and other constituents of the sterilant fluid remain behind as residue that builds up over time.

Therefore, a need exists that overcomes one or more of the disadvantages of present decontamination systems.

SUMMARY OF THE INVENTION

According to one aspect, this disclosure provides a decontamination system for a device. The decontamination system comprises a device container, a wicking pad, and a sterilant fluid delivery device. The device container defines a device receiving area. The wicking pad is in fluid communication with the device receiving area. The sterilant fluid delivery device is in fluid communication with the wicking pad. The sterilant fluid delivery device is configured to wet the wicking pad with sterilant fluid. The wicking pad is configured to evaporate sterilant fluid into the device receiving area.

According to another aspect, this disclosure provides a sterilant kit for a system to decontaminate a device. The sterilant kit includes a wicking pad dimensioned to be received in a device receiving area of a decontamination system. The wicking pad includes a sterilant fluid and is deposited thereon. The kit includes packaging containing the wicking pad. The packaging comprises an imperious material configured to prevent leakage of the sterilant fluid out of the packaging.

According to a further aspect, this disclosure provides a method of decontaminating a device. The method includes the step of providing a device decontamination system with a lumen container in fluid communication with a wicking pad. A sterilant fluid is delivered to the wicking pad. The method also includes decontaminating a device within the container by evaporating the sterilant fluid from the wicking pad.

BRIEF DESCRIPTION OF THE DRAWINGS

The present disclosure will be described hereafter with reference to the attached drawings which are given as non-limiting examples only, in which.

Figure 1:
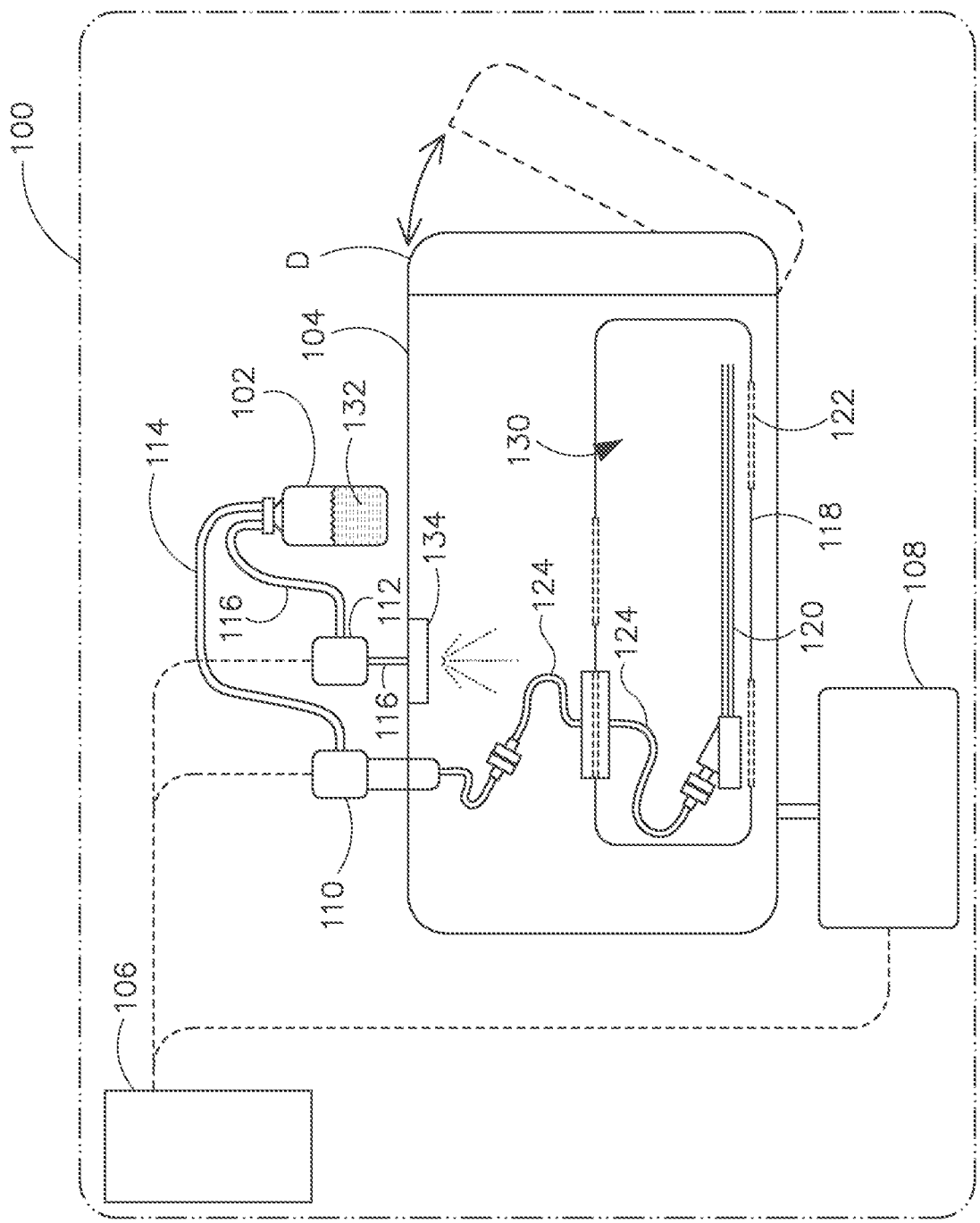
FIG. 1 is diagrammatic view of a system for decontaminating a medical device according to an embodiment of the present disclosure.

Corresponding reference characters indicate corresponding parts throughout the several views. The components in the figures are not necessarily to scale, emphasis instead being placed upon illustrating the principals of the invention. The exemplification set out herein illustrates embodiments of the invention, and such exemplification is not to be construed as limiting the scope of the invention in any manner.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

This disclosure relates to a wicking pad for delivering sterilant fluid in a decontamination system. In some embodiments, sterilant fluid is delivered to the wicking pad, and evaporates at a given pressure for delivering the fluid to a device to be decontaminated. Embodiments are also contemplated in which the wicking pad could come in a package in which the wicking pad is already pre-soaked with sterilant fluid. Depending on the circumstances, the evaporation of fluid from the wicking pad could be aided with pressurized air and/or a heating element. In some cases, the wicking pad can be oriented at a certain angle to ease distribution of the sterilant fluid along the entire surface of the pad.

FIG. 1 is a diagrammatic view of one embodiment of a system 100 for decontaminating a medical, dental, or other device. In some embodiments the device may have one or more lumens extending there-through. As shown, the system includes a reservoir 102, a decontamination chamber 104, a system controller 106, an environmental monitoring and control system 108, and a vaporizer 110 and a pump 112 which are connected to the reservoir 102 by conduits 114 and 116, respectively. In some embodiments, the vaporizer 110 and pump 112 may be optional depending on the circumstances. For example, in some embodiments, a wicking pad pre-soaked with sterilant fluid could be used to draw sterilant fluid through the device, such as a lumen device, with a circulation pump instead of using vaporizer 110 and pump 112. A terminal package 118 containing a lumen device 120 for decontamination may be placed within the decontamination chamber 104. In the illustrated embodiment, the terminal package 118 can include a plurality of openings or pores 122. The reservoir 102 may be in fluid communication with the decontamination chamber 104 via a wicking pad 134, which evaporates a sterilant fluid delivered by the pump 112 into the decontamination chamber 104. The reservoir 102 may also be in fluid communication with one or more lumens extending through the lumen device 120 via vaporizer 110 and fluid conduit 124.

The system controller 106 provides control signals to and/or receives condition sensing and equipment status signals from the reservoir 102, the decontamination chamber 104, environmental monitoring and control system 108, and/or the vaporizer 110 and pump 112. In some embodiments, the system 100 can be assembled in a device small enough to sit on a tabletop or counter. For example, the decontamination chamber 104 may have an interior volume of less than about ten cubic feet.

The lumen device 120 to be decontaminated can be placed into the decontamination chamber 104 by opening the door D and placing the device 120, such as a lumen device, on a rack or other supporting assembly in the interior of the decontamination chamber 104. In some embodiments, the device 120, such as a lumen device, may be enclosed in the terminal package 118 before being placed in the decontamination chamber 104. In the example shown, the terminal package 118 defines a lumen device receiving area 130 to receive the lumen device 120 for decontamination. In the illustrated embodiment, the terminal package 118 includes a plurality of openings or pores 122.

The reservoir 102 may be a holding tank or other assembly configured to hold a sterilant fluid 132. In some embodiments, the sterilant fluid 132 can be a chemical or other substance suitable for use in a sterilization process that complies with the International Organization for Standardization (ISO) standard ISO/TC 198, Sterilization of Healthcare Products and/or the Association for the Advancement of Medical Instrumentation (AAMI) standard ANSI/AAMI/ISO 11140-1:2005, "Sterilization of Healthcare Products—Chemical Indicators—Part I: General Requirements" (Arlington, Va.: AAMI 2005). In some embodiments, the sterilant fluid 132 can be at room temperature (e.g., 20° C. to 25° C.) substance that can be dispersed as a fluid, such as a liquid, a vapor, or a combination thereof (such as a fog) during the decontamination process. Suitable substances for the sterilant fluid 132 include hydrogen peroxide ($H_2O_2$) and peracetic acid (PAA). In various embodiments, the sterilant fluid is a composition that includes: (a) hydrogen peroxide; (b) organic acid; (c) a polymeric sulfonic acid resin based chelator; and (d) surfactant. The composition includes less than about 1 wt. % of an anticorrosive agent. The composition can further optionally include water.

In one aspect, the hydrogen peroxide present in the composition can be from about 0.5 wt. % to about 30 wt. %, from about 0.5 wt. % to about 1.5 wt. %, from about 0.8 wt. % to about 1.2 wt. %, from about 20 wt. % to about 30 wt. % and all ranges and values from about 0.5 wt. % to about 30 wt. %.

In another aspect, the acetic acid present in the composition can be from about 1 wt. % to about 25 wt. %, from about 4 wt. % to about 20 wt. %, from about 4.5 wt. % to about 5.5 wt. %, from about 9 wt. % to about 17 wt. % and all ranges and values from about 1 wt. % to about 25 wt. %.

In still another aspect, the peracetic acid present in the composition can be from about 0.01 wt. % to about 25 wt. %, from about 0.05 wt. % to about 20 wt. %, from about 0.05 wt. % to about 0.1 wt. %, from about 3.5 wt. % to about 8 wt. % and all ranges and values from about 0.01 wt. % to about 25 wt. %.

In yet another aspect, the polymeric resin chelator present in the composition can be from about 0.1 wt. % to about 5 wt. %, from about 0.2 wt. % to about 2 wt. %, from about 0.5 wt. % to about 1.5 wt. % and all ranges and value from about 0.1 wt. % to about 5 wt. %.

In various embodiments, the present invention provides for a composition that includes: (a) hydrogen peroxide, present in a concentration of about 0.5 wt. % to about 30 wt. %, e.g., about 28 wt. %; (b) acetic acid, present in a concentration of about 3 wt. % to about 25 wt. %, e.g., about 16 wt. %; (c) a sulfonic acid supported polymeric resin chelator present in a concentration of about 0.1 wt. % to about 5 wt. %, e.g., about 0.2 wt. % to about 0.7 wt. %; and, optionally, (d) Pluronic® 10R5 surfactant block copolymer, present in a concentration of about 2.0 wt. %, wherein the composition comprises less than about 0.1 wt. % of an anticorrosive agent, e.g., 0 wt. % of an anticorrosive agent. The composition can further optionally include water. In some embodiments, the hydrogen peroxide and acetic acid can combine to form peracetic acid, present in about 4 wt. % to about 8 wt. %, e.g., 6.8-7.5 wt. %.

In certain aspects, the peracetic acid/hydrogen peroxide compositions are stabilized without the need for a phosphonic based chelator, such as 1-hydroxyethylidene-1, 1,-diphosphonic acid. In other aspects, a phosphonic based chelator, such as 1-hydroxyethylidene-1, 1,-diphosphonic acid can be included in the sterilant fluid and therefore, component c), the polymeric sulfonic acid resin is optional.

The use of the polymeric stabilizer is detailed in pending PCT application PCT/US19/53090, filed Sep. 26, 2019, entitled "Peracetic Acid Stabilized Compositions with Polymeric Resins Chelators", the contents of which are incorporated herein by reference The terminal package 118 is sized so that the device 120 to be decontaminated, such as a lumen device, fits within the terminal package 118. In some embodiments, the terminal package 118 may be generally described as having a top, a bottom, and four sides extending between the top and bottom to create a cube-like structure. However, the terminal package 118 may have any suitable shape which encloses the device 120. In some embodiments, the terminal package 118 may be formed from a rigid material such that the terminal package 118 has a rigid or structured shape. Alternatively, the terminal package 118 may be formed from a flexible material such that the terminal package 118 has a flexible shape. Suitable materials for the terminal package 118 include but are not limited to a polymeric non-woven sheet, such as spun-bonded polyethylene (e.g., Tyvek®, sold by E.I. du Pont de Nemours and Company, Wilmington, Del.), and polymeric materials such as polyester and polypropylene. Suitable materials for terminal package 118 having a rigid or structured shape include but are not limited to various metals such as aluminum, stainless steel and/or various polymers in rigid form such as polyethylene and/or polypropylene.

The device 120 may be positioned within the terminal package 118 and subjected to one or more decontamination cycles. Suitable devices include any medical, dental or other device, including those having at least one lumen extending through at least a portion of the device. In some embodiments, the device 120 may include at least one lumen extending the entire length of the device. For example, the device 120 may be an endoscope.

The terminal package 118 may be configured to prevent or reduce microbes and/or other contaminants from entering the terminal package 118. In some embodiments, for example, the terminal package 118 can include a material suitable for allowing flow of a sterilant fluid, such as hydrogen peroxide ($H_2O_2$) and/or peracetic acid (PAA), into the device receiving area 130, such as a lumen device receiving area, of the terminal package 118 and blocking or reducing the flow of contaminants into the interior of the terminal package 118. In the illustrated embodiment, the terminal package 118 includes a plurality of openings or pores 122 for allowing flow of the sterilant fluid 132 into the terminal package 118. In some embodiments, the pores 122 may be sized so as to allow the sterilant fluid 132 and/or air to communicate into and out of the container 118 as well as prevent microbes from entering the terminal package 118.

In some embodiments, the sterilant fluid 132 can flow concurrently from the reservoir 102 to vaporizer 110 and pump 112 and subsequently to decontamination chamber 104 and lumen device 120. In other embodiments, the flow of the sterilant fluid 132 to vaporizer 110 may initiate before or after the initiation of flow of the sterilant fluid 132 to pump 112. The sterilant fluid 132 from vaporizer 110 may decontaminate the internal and/or external surfaces of the device 120 and the sterilant fluid 132 from the vaporizer 110 may delivered to a wicking pad to decontaminate the exterior surfaces of device 120 as well as the surfaces of the terminal package 118.

Although the wicking pad 134 is shown outside the terminal package 118, but inside decontamination chamber 104 for purposes of example, the wicking pad 134 could be positioned inside the terminal package 118 depending on the circumstances. The term "device container" is broadly intended to encompass any enclosure in which the device 120, such as a lumen device, may be received. In some cases, the device container could be considered the decontamination chamber 104 into which the device 120 is received. The device container could also be the terminal package 118 into which the device is received. Accordingly, depending on the circumstances, the wicking pad 134 could be received inside the device container, which could be either the decontamination chamber 104 and/or the terminal package 118.

The amount of sterilant fluid 132 introduced into the decontamination chamber 104, the device 120 or a combination thereof can be controlled by the system controller 106 by controlling the amount of the sterilant fluid 132 fed or delivered to vaporizer 110 and pump 112. The rate and amount of the sterilant fluid 132 delivered to vaporizer 110 and pump 112 may be preprogrammed into the system controller 106 or may be manually entered into the system controller 106 by a user of the system 100.

To decontaminate a device, such as a medical, dental or other device, specifically a lumen device, the device 120 may be sealed within the terminal package 118 and placed in the decontamination chamber 104. The device 120 is then subjected to a decontamination process which may include one or more decontamination cycles. A suitable cycle may include adjusting the pressure of the decontamination chamber 104 to a suitable range, such as to a pressure less than 10 Torr, conditioning using plasma, and introducing the sterilant fluid 132 into the decontamination chamber 104 via pump 112 and wicking pad 134 and introducing the sterilant fluid 132 into the device 120 via the vaporizer 110 and conduit 124. The sterilant fluid 132 may be held within the decontamination chamber 104 for a period of time to facilitate the decontamination of the device 120, and in particular, the exterior surfaces of the device 120. Similarly, the sterilant fluid 132 may be held within the lumen device 120 for a period of time to facilitate the decontamination of the interior surfaces or lumen(s) of the device 120. When the sterilant fluid 132 has been held in the decontamination chamber 104 for the desired or programmed amount of time, the system controller 106 can vent the decontamination chamber 104 to a higher, but sub-atmospheric pressure. The system controller 106 can then hold the pressure within the decontamination chamber 104 for a period of time to further facilitate the decontamination of the load. Following the hold period, the system controller 106 may evacuate the decontamination chamber 104 to remove the sterilant fluid residuals from the decontamination chamber 104 which may also include a plasma treatment to further enhance the removal of the substance residuals, followed by venting the decontamination chamber 104. This cycle or steps may be repeated or extended as part of a comprehensive cycle.

Figure 2:
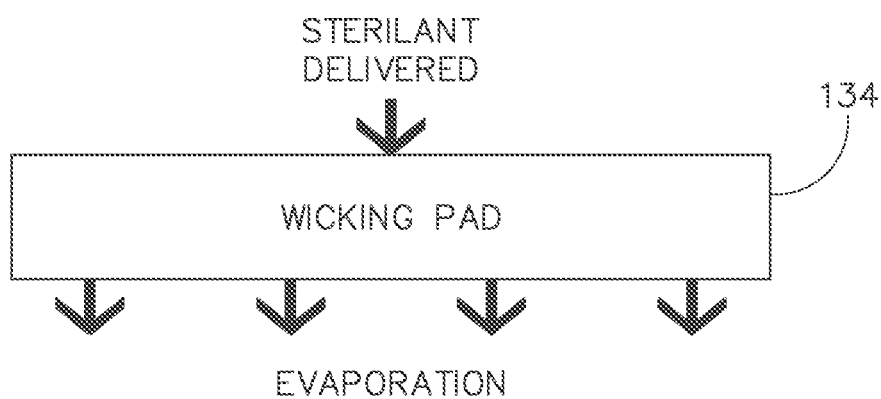
FIG. 2 is a side diagrammatic view of an example wicking pad according to an embodiment of the present disclosure.
Figure 5:
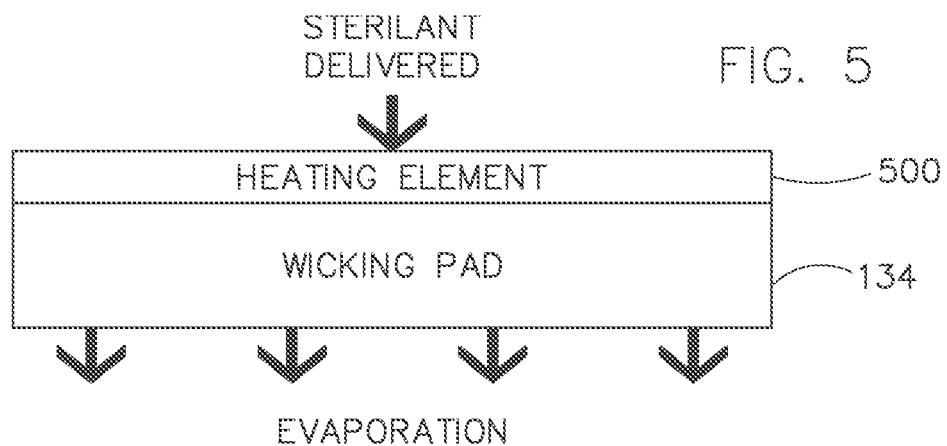
FIG. 5 is a side diagrammatic view of the wicking pad shown in FIG. 2 in use with a heating element according to an embodiment of the present disclosure.

FIG. 2 is a side diagrammatic view of the wicking pad 134 according to an embodiment of this disclosure. The wicking pad 134 works, broadly speaking, by increasing the surface area of a given amount of sterilant fluid, and in turn increasing the rate of evaporation. Evaporation is an endothermic process and can be accelerated if the surface area is increased or heat provided (FIG. 5).

Depending on the circumstances, the wicking pad 134 may be constructed of filter-like materials, such as cellulosic pads, fibrous pads, or open cell foam. In some cases, the wicking pad 134 could be constructed from a rigid microporous material, such that it is less prone to shed fibers or debris. In embodiments in which the wicking pad 134 is formed from very small, hollow tube fibers, this may aid in spreading out the sterilant fluid and increasing the surface area. The rate of evaporation will generally be increased as more wetted surface area is provided. Embodiments are contemplated in which the wicking pad 134 could be used in decontamination and/or sterilization methods that use ethylene oxide or low temperature methods, such as peracetic acid and hydrogen peroxide, hydrogen peroxide or formaldehyde based methods.

In some embodiments, such as the example shown in FIG. 1, the wicking pad 134 can be wetted by being in close proximity, or contact with, a tube 116 (or other fluid conduit) which a predetermined amount of sterilant fluid delivered by pump 112. Depending on the circumstances, the wicking pad 134 could be pre-wetted with sterilant fluid and placed in proximity of the device 120 within the decontamination chamber 104 so that sterilant vapor can be drawn through the device 120, such as with a circulation pump. The decontamination process would then provide conditions within the decontamination chamber 104 and/or terminal package 118 (depending on the location of the wicking pad 134) conductive to evaporation of the sterilant fluid. The constituents of the sterilant fluid which are able to vaporize at the given pressure leave the wicking pad 134 in the form of vapor while the remaining constituents are left behind. This property may be particularly useful to leave behind a chelating agent or other stabilizer present in the sterilant fluid but not able to vaporize. This is valuable because these stabilizers would otherwise be aerosolized with a nozzle, which coat surfaces of the system 100 or sensors, and then remain behind as residue, which could build up over time.

Figure 3:
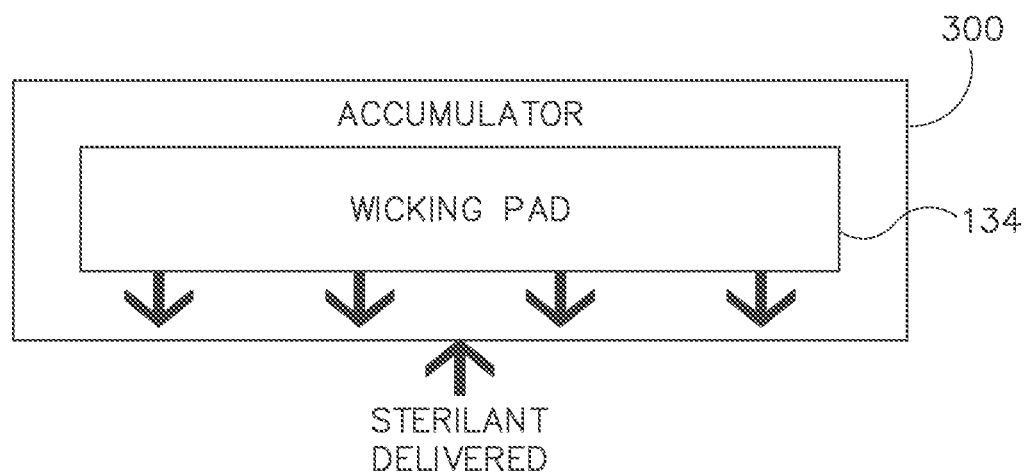
FIG. 3 is a side diagrammatic view of the wicking pad shown in FIG. 2 in use with an accumulator pump according to an embodiment of the present disclosure.

FIG. 3 shows a diagrammatic view of an embodiment in which the wicking pad 134 is used in conjunction with an accumulator pump 300. For example, in some cases the accumulator pump 300 could be a vacuum operated accumulator that is in fluid communication with the decontamination chamber 104 and/or the terminal package 118. In some such embodiments, the accumulator pump 300 could have sterilant fluid sprayed into it, in a fine mist or large droplet manner. If the wicking pad 134 is disposed within the accumulator pump 300, as shown in the example of FIG. 3, spraying sterilant fluid into the accumulator pump 300 would wet the wicking pad 134. When a vacuum cycle is performed with the accumulator pump 300, this would vaporize sterilant fluid in the wicking pad 134 and enhance sterilant fluid delivered by the accumulator pump 300. This would allow for a potentially thinner wicking pad 134 that still achieves a relatively uniform level of fluid distribution across its width. It is believed that a thinner wicking pad 134 would offer more resistance to spreading out of fluid across the width.

Figure 4:
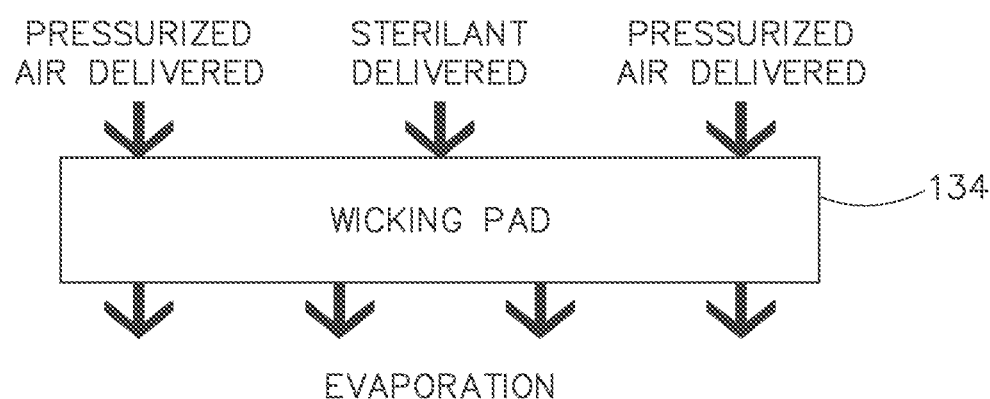
FIG. 4 is a side diagrammatic view of the wicking pad shown in FIG. 2 in use with a pressurized air source according to an embodiment of the present disclosure.

FIG. 4 shows a diagrammatic view of an embodiment in which the wicking pad 134 is used in conjunction with a pressurized air source. The wicking pad 134 does not require a pressurized air source to operate. This can be an advantage because air is often detrimental to a low temperature vaporization process since the air added can raise the pressure in the decontamination chamber 104, and increase pressure leads to a reduced rate of vaporization. However, in instances where added air is feasible, pressurized air may optionally be added to increase the rate of evaporation. In some cases, as shown in FIG. 4, air may be directed through the wicking pad 134; however, in other embodiments, air could be directed towards a side or front of the wicking pad 134 depending on the circumstances. There are a variety of devices that could be used to direct air towards the wicking pad 134, including but not limited to compressed air cartridge, a fan, and/or a blower.

FIG. 5 shows an embodiment in which a heating element 500 is associated with the wicking pad 134. For example, in some embodiments, at least a portion of the wicking pad 134 may be heated by a heating element 500, such as a hot plate. The temperature of the fluid can affect the rate of evaporation. Thus, heating the wicking pad 134, and sterilant fluid it contains, may help to accelerate the evaporation process.

Figure 6:
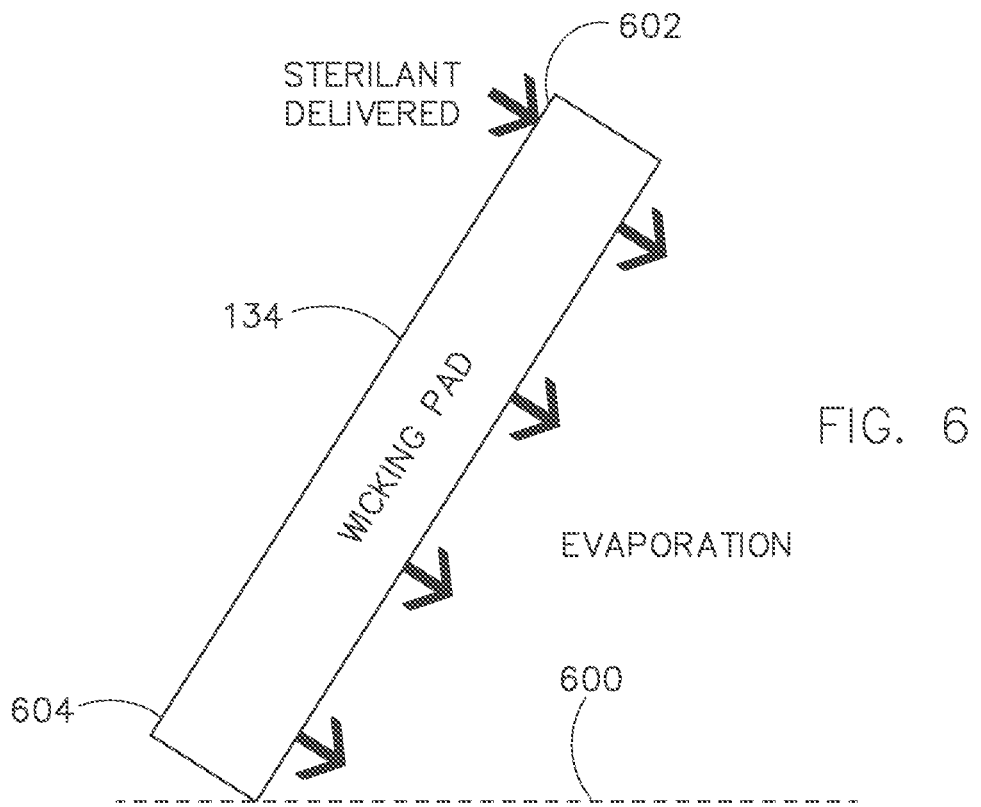
FIG. 6 is a side diagrammatic view of the wicking pad shown in FIG. 2 in an angled environment according to an embodiment of the present disclosure.

FIG. 6 shows an embodiment in which the wicking pad 134 is positioned at an angle with respect to a horizontal axis 600. As shown, sterilant fluid is delivered at a first end 602 of the wicking pad 134. Due to the orientation of the wicking pad 134, the sterilant fluid flows via gravity feed towards a second end 604 to distribute sterilant fluid through the wicking pad 134. The angle at which the wicking pad 134 is positioned (with gravity effect) may help to uniformly distribute the sterilant fluid across the wicking pad 134.

Figure 7:
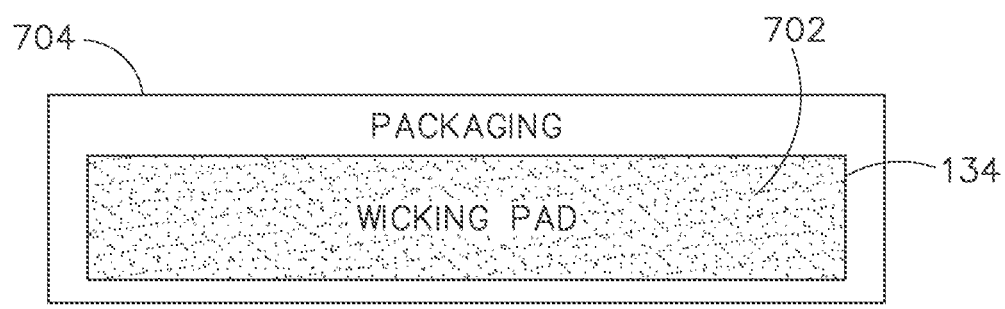
FIG. 7 is a side diagrammatic view of a pre-soaked wicking pad package according to an embodiment of the present disclosure.

FIG. 7 shows an embodiment in which the wicking pad 134 is "pre-soaked" with sterilant fluid 700. For example, in some cases, the wicking pad 134 could be in packaging 704 and "pre-soaked" with a sterilant fluid. The packaging 704 would be formed from a fluid imperious material to prevent leakage of the sterilant fluid out of the packaging 704. This would allow the wicking pad 134 to conveniently be sold as a single-use item and reduce complexity of the overall sterilization system 100.

EXAMPLES

Illustrative examples of the method and system disclosed herein are provided below. An embodiment of the method and system may include any one or more, and any combination of, the examples described below.

Example 1 is a decontamination system for a device, such as a lumen device. The decontamination system comprises a device container, a wicking pad, and a sterilant fluid delivery device. The device container defines a device receiving area. The wicking pad is in fluid communication with the device receiving area. The sterilant fluid delivery device is in fluid communication with the wicking pad. The sterilant fluid delivery device is configured to wet the wicking pad with sterilant fluid. The wicking pad is configured to evaporate sterilant fluid into the device receiving area.

In Example 2, the subject matter of Example 1 is further configured such that the sterilant fluid delivery device comprises a pump configured to deliver sterilant fluid to the wicking pad.

In Example 3, the subject matter of Example 1 is further configured such that the sterilant fluid delivery device comprises a vacuum operated accumulator configured to deliver sterilant fluid to the wicking pad. In some cases, the vacuum operated accumulator is disposed in the device receiving area.

In Example 4, the subject matter of Example 1 is further configured such that the device container comprises one or more of a terminal package or a decontamination chamber.

In Example 5, the subject matter of Example 1 is further configured such that the wicking pad comprises one or more of a cellulosic pad, fibrous pad, and/or an open cell foam.

In Example 6, the subject matter of Example 1 is further configured such that the wicking pad comprises one or more of a rigid microporous material.

In Example 7, the subject matter of Example 1 is further configured such that the sterilant fluid is configured to evaporate from the wicking pad at a predetermined pressure within the device container.

In Example 8, the subject matter of Example 1 is further configured to include a blower configured to direct air flow towards the wicking pad.

In Example 9, the subject matter of Example 1 is further configured such that the wicking pad includes a first end and a second end and the sterilant fluid delivery device is configured to introduce sterilant fluid at the first end of the wicking pad.

In Example 10, the subject matter of Example 9 is further configured such that the wicking pad is angled to distribute sterilant fluid introduced at the first end towards the second end via gravity effect.

In Example 11, the subject matter of Example 1 is further configured to include a heating element configured to apply heat to the wicking pad.

Example 12 is a sterilant kit for a system to decontaminate a device. The sterilant kit includes a wicking pad dimensioned to be received in a device receiving area of a decontamination system. The wicking pad includes a sterilant fluid that is deposited thereon. The kit includes packaging containing the wicking pad. The packaging comprises an imperious material configured to prevent leakage of the sterilant fluid out of the packaging.

In Example 13, the subject matter of Example 12 is further configured such that the sterilant fluid comprises one or more of peracetic acid, hydrogen peroxide, and/or formaldehyde.

In Example 14, the subject matter of Example 12 is further configured such that the wicking pad comprises one or more of a cellulosic pad, fibrous pad, and/or an open cell foam.

In Example 15, the subject matter of Example 12 is further configured such that the wicking pad comprises one or more of a rigid microporous material.

In Example 16, the subject matter of Example 16 is further configured such that the sterilant fluid is configured to evaporate from the wicking pad at a predetermined pressure.

Example 17 is a method of decontaminating a device. The method includes the step of providing a device decontamination system with a container in fluid communication with a wicking pad. A sterilant fluid is delivered to the wicking pad. The method also includes decontaminating a device within the container by evaporating the sterilant fluid from the wicking pad.

In Example 18, the subject matter of Example 17 is further configured such that the delivering step includes operating a pump in fluid communication with the wicking pad.

In Example 19, the subject matter of Example 17 is further configured such that the delivering step includes introducing a vacuum to an evaporator device in fluid communication with the wicking pad.

In Example 20, the subject matter of Example 17 is further configured to include the step of heating the wicking pad.

Although the present disclosure has been described with reference to particular means, materials and embodiments, from the foregoing description, one skilled in the art can easily ascertain the essential characteristics of the invention and various changes and modifications may be made to adapt the various uses and characteristics without departing from the spirit and scope of the invention.

What is claimed is:

1. A decontamination system for a device, the decontamination system comprising:
   a device container defining a device receiving area;
   a wicking pad located in the device container and in fluid communication with the device receiving area;
   a sterilant fluid delivery device in fluid communication with the wicking pad, the sterilant fluid delivery device comprising a vacuum operated accumulator pump in fluid communication with the wicking pad, wherein the vacuum operated accumulator pump is disposed in the device receiving area, and wherein the sterilant fluid delivery device is configured to wet the wicking pad with sterilant fluid; and
   wherein the wicking pad is configured to evaporate sterilant fluid into the device receiving area.

2. The decontamination system of claim 1, wherein the device container comprises one or more of a terminal package or a decontamination chamber.

3. The decontamination system of claim 1, wherein the wicking pad comprises one or more of a cellulosic pad, fibrous pad, and/or an open cell foam.

4. The decontamination system of claim 1, wherein the wicking pad comprises one or more of a rigid microporous material.

5. The decontamination system of claim 1, wherein the sterilant fluid is configured to evaporate from the wicking pad at a predetermined pressure within the device container.

6. The decontamination system of claim 1, further comprising a blower configured to direct air flow towards the wicking pad.

7. The decontamination system of claim 1, wherein the wicking pad includes a first end and a second end and the sterilant fluid delivery device is configured to introduce sterilant fluid at the first end of the wicking pad.

8. The decontamination system of claim 7, wherein the wicking pad is angled to distribute sterilant fluid introduced at the first end towards the second end via gravity effect.

9. The decontamination system of claim 1, further comprising a heating element configured to apply heat to the wicking pad.

10. A decontamination system for a device, the decontamination system comprising:
    a device container defining a device receiving area;
    a wicking pad located in the device container and in fluid communication with the device receiving area;
    a sterilant fluid delivery device in fluid communication with the wicking pad, wherein the sterilant fluid delivery device is configured to wet the wicking pad with sterilant fluid; and
    a blower configured to direct air flow towards the wicking pad;
    wherein the wicking pad is configured to evaporate sterilant fluid into the device receiving area.

11. The decontamination system of claim 10, wherein the device container comprises one or more of a terminal package or a decontamination chamber.

12. The decontamination system of claim 10, wherein the sterilant fluid delivery device comprises a pump configured to deliver sterilant fluid to the wicking pad.

13. The decontamination system of claim 10, wherein the wicking pad comprises one or more of a cellulosic pad, fibrous pad, and/or an open cell foam.

14. The decontamination system of claim 10, wherein the wicking pad comprises one or more of a rigid microporous material.

15. The decontamination system of claim 10, further comprising a heating element configured to apply heat to the wicking pad.

16. A decontamination system for a device, the decontamination system comprising:
    a device container defining a device receiving area;
    a wicking pad located in the device container and in fluid communication with the device receiving area;
    a heating element configured to apply heat to the wicking pad;

a sterilant fluid delivery device in fluid communication with the wicking pad wherein the sterilant fluid delivery device is configured to wet the wicking pad with sterilant fluid; and wherein the wicking pad is configured to evaporate sterilant fluid into the device receiving area.

17. The decontamination system of claim 16, wherein the sterilant fluid delivery device comprises a pump configured to deliver sterilant fluid to the wicking pad.

18. The decontamination system of claim 16, wherein the device container comprises one or more of a terminal package or a decontamination chamber.

19. The decontamination system of claim 16, wherein the wicking pad comprises one or more of a cellulosic pad, fibrous pad, and/or an open cell foam.

20. The decontamination system of claim 16, wherein the wicking pad comprises one or more of a rigid microporous material.

\* \* \* \* \*